(12) United States Patent
Gillies et al.

(10) Patent No.: US 11,786,156 B2
(45) Date of Patent: Oct. 17, 2023

(54) METHOD AND APPARATUS FOR USE IN DETECTING MALINGERING BY A FIRST SUBJECT IN TESTS OF PHYSICAL AND/OR MENTAL FUNCTION OF THE FIRST SUBJECT

(71) Applicant: KONINKLIJKE PHILIPS N.V., Eindhoven (NL)

(72) Inventors: Murray Fulton Gillies, Eindhoven (NL); Reza Sharifi Sedeh, Malden, MA (US); Daisy Van Minde, Eindhoven (NL)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 412 days.

(21) Appl. No.: 16/756,635

(22) PCT Filed: Dec. 13, 2018

(86) PCT No.: PCT/EP2018/084650
§ 371 (c)(1),
(2) Date: Apr. 16, 2020

(87) PCT Pub. No.: WO2019/115658
PCT Pub. Date: Jun. 20, 2019

(65) Prior Publication Data
US 2020/0323475 A1    Oct. 15, 2020

Related U.S. Application Data

(60) Provisional application No. 62/598,128, filed on Dec. 13, 2017.

(30) Foreign Application Priority Data

Jun. 8, 2018 (EP) .................................... 18176671

(51) Int. Cl.
*A61B 5/16* (2006.01)
*G16H 50/30* (2018.01)
*A61B 5/00* (2006.01)

(52) U.S. Cl.
CPC .............. *A61B 5/16* (2013.01); *A61B 5/7275* (2013.01); *A61B 5/74* (2013.01); *G16H 50/30* (2018.01)

(58) Field of Classification Search
CPC ........... A61B 5/16; A61B 5/74; A61B 5/7275; G16H 50/30
See application file for complete search history.

(56) References Cited

U.S. PATENT DOCUMENTS 8,346,331 B2   1/2013  Bunce et al.
2003/0167149 A1*  9/2003  Simon .................... A61B 5/165
                                                                702/182

(Continued)

OTHER PUBLICATIONS

Scott, C.L., "The Assessment of Malingering—An Evidence-Based Approach". University of California, Mar. 16, 2016.

(Continued)

*Primary Examiner* — Lynsey C Eiseman
*Assistant Examiner* — Jessandra F Hough

(57) ABSTRACT

According to an aspect, there is provided an apparatus for use in detecting malingering by a first subject in a test of physical and/or mental function of the first subject. The apparatus comprises a memory unit configured to store a plurality of models, each model identifies a respective set of physical and/or mental function tests from a plurality of different physical and/or mental function tests that can be used to detect malingering in a subject and that meets one or more possible user requirements for detecting malingering; and a processing unit configured to receive a user input from a user of the apparatus, the received user input indicating a user requirement for detecting malingering in the first sub- (Continued)

ject; following receipt of an indication that the first subject may be malingering in one or more physical and/or mental function tests, retrieve, from the memory unit, the identity of a first set of physical and/or mental function tests for a model that meets the indicated user requirement; and output a control signal to a function testing device indicating the retrieved identity of the first set of physical and/or mental function tests such that the testing device provides the identified first set of physical and/or mental function tests to the first subject completion for completion.

19 Claims, 4 Drawing Sheets

(56) References Cited

U.S. PATENT DOCUMENTS

| | | |
|---|---|---|
| 2005/0273017 A1 | 12/2005 | Gordon |
| 2015/0245789 A1 | 9/2015 | Dromerick et al. |
| 2016/0022136 A1 | 1/2016 | Barry et al. |
| 2016/0213298 A1* | 7/2016 | Elsmore .................. A61B 5/165 |

OTHER PUBLICATIONS

Schnupp, T. et al., "Detection of Malingering in Dizzy Patients Utilizing Adaptive Pattern Recognition". Biomed Tech 2012; 57(Suppl. 1) 2012 by Walter de Gruyter, DOI: 10.1515/bmt-2012-4490.

Lezak, M.D. et al., "Neuropsychological assessment". (2004) Oxford University Press.

Woods, L.D. et al., "Computerized analysis of error patterns in digit span recall". Journal of Clinical and Experimental Neuropsychology. 2011, 33 (7), Abstract.

Meyers, J.E. et al., "Detection of Malingerers Usin the Ray Complex Figure and Recognition Trial". Applied Neuropsychology 1999, 6(4), Abstract.

Meyers, J.E. et al., "A validation of multiple malingering detection methods in a large clinical sample". Archives of Clinical Neuropsychology 2003 (18) 261-276.

Mittenberg, W. et al., "Base Rates of Malingering and Symptom Exeggeration". J Clin Exp Neuropsychology 2002 (24): Abstract.

MacNeill, A. et al., "Brief Communication: Trail Making Test and Malingering among Substance Abusers". Int J Neuroscience 2002, 112(12) Abstract.

International Search Report for PCT/EP2018/084650 dated Dec. 13, 2018.

* cited by examiner

Digit span – result for subject A

| Item | Order | Response | Score | Item score |
|---|---|---|---|---|
| 1 | 4-8-5 | 4-8-5 | 1 | 2 |
| | 2-6-8 | 2-6-8 | 1 | |
| 2 | 5-7-2-4 | 5-7-2-4 | 1 | 1 |
| | 7-6-2-9 | x7-6-9-2 | 0 | |
| 3 | 4-7-1-5-9 | 4-7-1-5-9 | 1 | 2 |
| | 2-8-3-6-9 | 2-8-3-6-9 | 1 | |
| 4 | 8-3-7-1-4-2 | 8-3-7-1-4-2 | 1 | 2 |
| | 7-8-4-9-3-6 | 7-8-4-9-3-6 | 1 | |
| 5 | 8-2-1-9-3-7-4 | 8-2-1-9-3-7-4 | 1 | 2 |
| | 2-9-5-4-9-6-8 | 2-9-5-4-9-6-8 | 1 | |

Test score

Total score — 16

Forward score
| Score | 9 |
| Stopwatch time | 180 s |

Backward score
| Score | 7 |
| Stopwatch time | 175 s |

| Digit Span | DMI 80/100 |

Fig. 3

Test results for subject A

| | | | | | User's opinion on whether malingering is present |
|---|---|---|---|---|---|
| | | | | | X% |

Digit Span — P1 P2 P3 P4 P5
Verbal Fluency — P1 P2 P3 P4 P5
Trail making — P1 P2 P3 P4 P5
Rey-O — P1 P2 P3 P4 P5
O-search — P1 P2 P3 P4 P5
WCS — P1 P2 P4 P4 P5

DMI
23/100

Fig. 4

METHOD AND APPARATUS FOR USE IN DETECTING MALINGERING BY A FIRST SUBJECT IN TESTS OF PHYSICAL AND/OR MENTAL FUNCTION OF THE FIRST SUBJECT

CROSS-REFERENCE TO PRIOR APPLICATIONS

This application is the U.S. National Phase application under 35 U.S.C. §371 of International Application No. PCT/EP2018/084650, filed on Dec. 13, 2018, which claims the benefit of U.S. Patent Application No. 62/598,128, filed on Dec. 13, 2017 and European Patent Application No. EP18176671.8, filed on Jun. 8, 2018. These applications are hereby incorporated by reference herein.

FIELD OF THE INVENTION

The disclosure relates to the detection of malingering by a subject, and in particular to a method and apparatus for use in detecting malingering by a subject in tests of physical and/or mental function of the subject.

BACKGROUND OF THE INVENTION

Clinical neuropsychology is the field of determining the cognitive functioning of a person by requiring them to perform various validated neuropsychological tests and, for example, scoring their ability to perform these tests against norm scores that are representative for healthy individuals of a comparable demographic.

Assessing cognitive functioning is relevant for various patient groups including dementia, stroke, traumatic brain injury, multiple sclerosis, depression, epilepsy and schizophrenia as well as for screening healthy populations. Due to the ageing population and the rapidly increasing prevalence of some of these diseases there is an increasing recognition of the importance of cognitive functioning and that it is necessary to be able to perform a neuropsychological assessment in an efficient and reproducible manner.

In current clinical practice, neuropsychological tests are typically either (i) paper-pencil tests, where the patient is asked to draw an object on paper or to complete a pre-defined task which has been printed on the paper; (ii) auditory verbal tests, where the patient is asked to recall facts, number sequences or word groups and from these responses a score is calculated; and (iii) motor tasks where the patient is asked to complete a task that involves a physical activity such completing a puzzle or finger tapping.

According to current standard procedures, for a full neuropsychological assessment there are typically 30-40 individual tests that require up to 8 hours to be taken and analyzed by a qualified healthcare professional.

Malingering is where a person intentionally underperforms in physical and/or mental function tests to fabricate or exaggerate symptoms of a physical condition and/or a mental condition, and is a common issue with neuropsychological assessments. It is important to recognize this intentional under performance so that subjects who are trying to deceive can be identified. For example, subjects with suspected traumatic brain injury may have an incentive to malinger due to a litigation case, where a poor performance in cognitive tests would help the subjects' case in court. The same applies where a subject has (or appears to have) a physical injury.

Therefore, as well as the cognitive tests for the actual cognitive assessment, there is often also a test added to detect whether people are genuinely attempting to perform the test at the best of their cognitive abilities. An example of such a test would be the F-score in the Minnesota Multiphasic Personality Inventory (MMPI). This is referred to as a malingering test and when someone is intentionally underperforming they are referred to as a malingerer. In one survey, it was estimated that some degree of symptom exaggeration occurs in 39% of mild head injury cases, in 30% of disability assessments, and in 29% of personal injury cases.

The detection of malingering in neuropsychological tests (and other mental function tests, as well as physical function tests) is therefore a very important aspect for both the clinical practitioner and the court of law. However, malingering is often very difficult to detect based on individual test scores and people may have very advanced strategies in order to deceive the assessor. There are various publications that describe how detailed analysis of the responses to specific tests can yield more information to help identify a malingerer from amongst genuine performances. These include examining the type of errors and sequence location in a digit span, Memory Error Patterns (MEPs) in the Rey-O complex figure test, or the Trail Making Test (TMT) A/B ratio together with the individual TMT trial time. It is considered that inconsistency in performance levels between a subject's performance and report of impairment is the most common indicator of malingering.

SUMMARY OF THE INVENTION

One problem in detecting malingering (whether in mental function or physical function tests) is that the complex patterns in the tests that have to be assessed in order to detect a malingerer cannot always be done reliably "on the fly" (i.e. as they happen) by the assessor. It is therefore typically only possible to do this retrospectively after the assessment has been completed, or by adding specific malingering tests to the test battery (i.e. a set of tests to be performed) which adds time to the assessment. This represents a waste of resources since the neuropsychologist would probably have either abandoned the battery of tests had they known that the subject was malingering or perhaps even adapted the test battery to collect more evidence.

Another problem is the complexity of the analysis of the 30-40 tests to be able to establish that a subject is malingering. This analysis may show clear malingering in some tests but not in others. It is therefore time consuming and costly to come to a conclusion.

It is an object of the present invention to provide improved apparatuses and methods to address one or more of the above problems.

According to a first specific aspect, there is provided an apparatus for use in detecting malingering by a first subject in a test of physical and/or mental function of the first subject, the apparatus comprising a memory unit configured to store a plurality of models, each model identifies a respective set of physical and/or mental function tests from a plurality of different physical and/or mental function tests that can be used to detect malingering by a subject and that meets one or more possible user requirements for detecting malingering; and a processing unit configured to receive a user input from a user of the apparatus, the received user input indicating a user requirement for detecting malingering by the first subject; following receipt of an indication that the first subject may be malingering in one or more physical and/or mental function tests, retrieve, from the memory unit, the identity of a first set of physical and/or mental function tests for a model in the plurality of models that meets the indicated user requirement; and output a control signal to a testing device indicating the retrieved identity of the first set of physical and/or mental function tests such that the testing device provides the identified first set of physical and/or mental function tests to the first subject for completion. Thus, the first aspect provides an apparatus that allows a user (e.g. neuropsychologist) to specify their requirements for detecting whether a first subject is malingering (e.g. balancing the additional test burden on the first subject against the reliability of the malingering assessment), and for a suitable set of additional physical and/or mental function tests to be provided to the first subject if there is a suggestion that the first subject is malingering. In this way, the additional test burden on the first subject is only incurred when malingering is suspected.

In some embodiments, the one or more possible user requirements comprises a level of reliability of detecting malingering and/or a number of physical and/or mental function tests in a set.

In some embodiments, the indication that the first subject may be malingering in the physical and/or mental function test is received from the user of the apparatus. In other embodiments, the indication that the first subject may be malingering in the physical and/or mental function test is received from the testing device. In yet other embodiments, the processing unit can be configured to receive the indication that the first subject may be malingering by receiving a signal from the testing device relating to the completion of a physical and/or mental function test by the first subject; and processing the received signal to detect whether the first subject may be malingering. These embodiments provide different ways for the malingering indication to be received.

In some embodiments, the processing unit is further configured to receive results for the first subject in completing the first set of physical and/or mental function tests; analyse the results to determine values for one or more parameters relating to the completion of each physical and/or mental function test in the first set by the first subject; and process the determined values to determine an indication of whether the first subject is malingering in one or more of the physical and/or mental function tests in the first set. Thus, these embodiments provide that the apparatus is both for setting the tests to detect malingering and analysing the results to determine if malingering is present.

In some embodiments, the processing unit is further configured to receive population information relating to a plurality of subjects, the population information comprising results for the plurality of subjects in completing the plurality of different physical and/or mental function tests and an indication of whether the subject was malingering; and process the received population information to determine the plurality of models. This embodiment provides that the models can be determined based on population information which can enable the models to be more reliable in detecting malingering in line with the indicated user requirement.

In some embodiments, the processing unit is further configured to receive user requirement information indicating a range of possible user requirements; and process the received population information and the received user requirement information to determine the plurality of models. In this way models will be available that cover different user requirements.

In some embodiments, the processing unit is configured to process the received population information to determine the plurality of models using one or more artificial intelligence algorithms and/or one or more machine learning algorithms.

In some embodiments, the processing unit is further configured to, in response to an indication indicating that the identified first set of physical and/or mental function tests did not detect whether the first subject is malingering, prompt the user of the apparatus to indicate a different user requirement for detecting malingering in the first subject; in response to receiving an indication of a different user requirement from the user, retrieve, from the memory unit, the identity of a second set of physical and/or mental function tests for a model in the plurality of models that meets the indicated different user requirement; and output a control signal to the testing device indicating the retrieved identity of the second set of physical and/or mental function tests such that the testing device provides the identified second set of physical and/or mental function tests to the first subject for completion to detect whether the first subject is malingering. In this way, the apparatus can automatically adapt the testing process to detect malingering if an initial set of physical and/or mental function tests (the first set) did not provide a conclusion on whether the first subject is malingering.

In some embodiments, the processing unit is further configured to, in response to an indication indicating that the identified first set of physical and/or mental function tests did not detect whether the first subject is malingering, determine that a difficulty level of one or more of the physical and/or mental function tests in the first set of physical and/or mental function tests is to be increased; and output a control signal to the physical and/or mental function testing device indicating the identity of the first set of physical and/or mental function tests and the increased difficulty level such that the testing device provides the identified first set of physical and/or mental function tests to the first subject for completion to detect whether the first subject is malingering. In this way, the apparatus can automatically adapt the testing process to detect malingering if an initial set of physical and/or mental function tests (the first set) did not provide a conclusion on whether the first subject is malingering.

In some embodiments, the apparatus further comprises the testing device.

In some embodiments, the physical and/or mental function test(s) is/are cognitive function test(s).

According to a second specific aspect, there is provided a computer-implemented method for use in detecting malingering by a first subject in a test of physical and/or mental function of the first subject, the method in a processing unit comprising: storing a plurality of models in a memory unit, each model identifies a respective set of physical and/or mental function tests from a plurality of different physical and/or mental function tests that can be used to detect malingering in a subject and that meets one or more possible user requirements for detecting malingering; receiving a user input from a user, the received user input indicating a user requirement for detecting malingering by the first subject; following receipt of an indication that the first subject may be malingering in one or more physical and/or mental function tests, retrieving, from the memory unit, the identity of a first set of physical and/or mental function tests for a model in the plurality of models that meets the indicated user requirement; and outputting a control signal to a testing device indicating the retrieved identity of the first set of physical and/or mental function tests such that the testing device provides the identified first set of physical and/or mental function tests to the first subject for completion. Thus, the second aspect provides a method that allows a user (e.g. neuropsychologist) to specify their requirements for detecting whether a first subject is malingering (e.g. balancing the additional test burden on the first subject against the reliability of the malingering assessment), and for a suitable set of additional physical and/or mental function tests to be provided to the first subject if there is a suggestion that the first subject is malingering. In this way, the additional test burden on the first subject is only incurred when malingering is suspected.

In some embodiments, the one or more possible user requirements comprises a level of reliability of detecting malingering and/or a number of physical and/or mental function tests in a set.

In some embodiments, the indication that the first subject may be malingering in the physical and/or mental function test is received from the user. In other embodiments, the indication that the first subject may be malingering in the physical and/or mental function test is received from the testing device. In yet other embodiments, a signal can be received from the testing device relating to the completion of a physical and/or mental function test by the first subject; and the received signal can be processed to detect whether the first subject may be malingering. These embodiments provide different ways for the malingering indication to be received.

In some embodiments, the method further comprises receiving results for the first subject in completing the first set of physical and/or mental function tests; analysing the results to determine values for one or more parameters relating to the completion of each physical and/or mental function test in the first set by the first subject; and processing the determined values to determine an indication of whether the first subject is malingering in one or more of the physical and/or mental function tests in the first set. Thus, these embodiments provide that the method is both for setting the tests to detect malingering and analysing the results to determine if malingering is present.

In some embodiments, the method further comprises receiving population information relating to a plurality of subjects, the population information comprising results for the plurality of subjects in completing the plurality of different physical and/or mental function tests and an indication of whether the subject was malingering; and processing the received population information to determine the plurality of models. This embodiment provides that the models can be determined based on population information which can enable the models to be more reliable in detecting malingering in line with the indicated user requirement.

In some embodiments, the method further comprises receiving user requirement information indicating a range of possible user requirements; and processing the received population information and the received user requirement information to determine the plurality of models. In this way models will be available that cover different user requirements.

In some embodiments, the method comprises processing the received population information to determine the plurality of models using one or more artificial intelligence algorithms and/or one or more machine learning algorithms.

In some embodiments, the method comprises, in response to an indication indicating that the identified first set of physical and/or mental function tests did not detect whether the first subject is malingering, prompting the user to indicate a different user requirement for detecting malingering in the first subject; in response to receiving an indication of a different user requirement from the user, retrieving, from the memory unit, the identity of a second set of physical and/or mental function tests for a model in the plurality of models that meets the indicated different user requirement; and outputting a control signal to the testing device indicating the retrieved identity of the second set of physical and/or mental function tests such that the testing device provides the identified second set of physical and/or mental function tests to the first subject for completion. In this way, the method can automatically adapt the testing process to detect malingering if an initial set of physical and/or mental function tests (the first set) did not provide a conclusion on whether the first subject is malingering.

In some embodiments, the method further comprises, in response to an indication indicating that the identified first set of physical and/or mental function tests did not detect whether the first subject is malingering, determining that a difficulty level of one or more of the physical and/or mental function tests in the first set of physical and/or mental function tests is to be increased; and outputting a control signal to the testing device indicating the identity of the first set of physical and/or mental function tests and the increased difficulty level such that the testing device provides the identified first set of physical and/or mental function tests to the first subject for completion. In this way, the method can automatically adapt the testing process to detect malingering if an initial set of physical and/or mental function tests (the first set) did not provide a conclusion on whether the first subject is malingering.

In some embodiments, the physical and/or mental function test(s) is/are cognitive function test(s).

According to a third aspect, there is provided a computer program product comprising a computer readable medium having computer readable code embodied therein, the computer readable code being configured such that, on execution by a suitable computer or processor, the computer or processor is caused to perform the method according to the second aspect and any embodiment thereof.

These and other aspects will be apparent from and elucidated with reference to the embodiment(s) described hereinafter.

BRIEF DESCRIPTION OF THE DRAWINGS

Exemplary embodiments will now be described, by way of example only, with reference to the following drawings, in which:

FIG. 3 shows a set of results for a cognitive function test; and

FIG. 4 shows a set of results for different cognitive function tests.

DETAILED DESCRIPTION OF EMBODIMENTS

Figure 1:
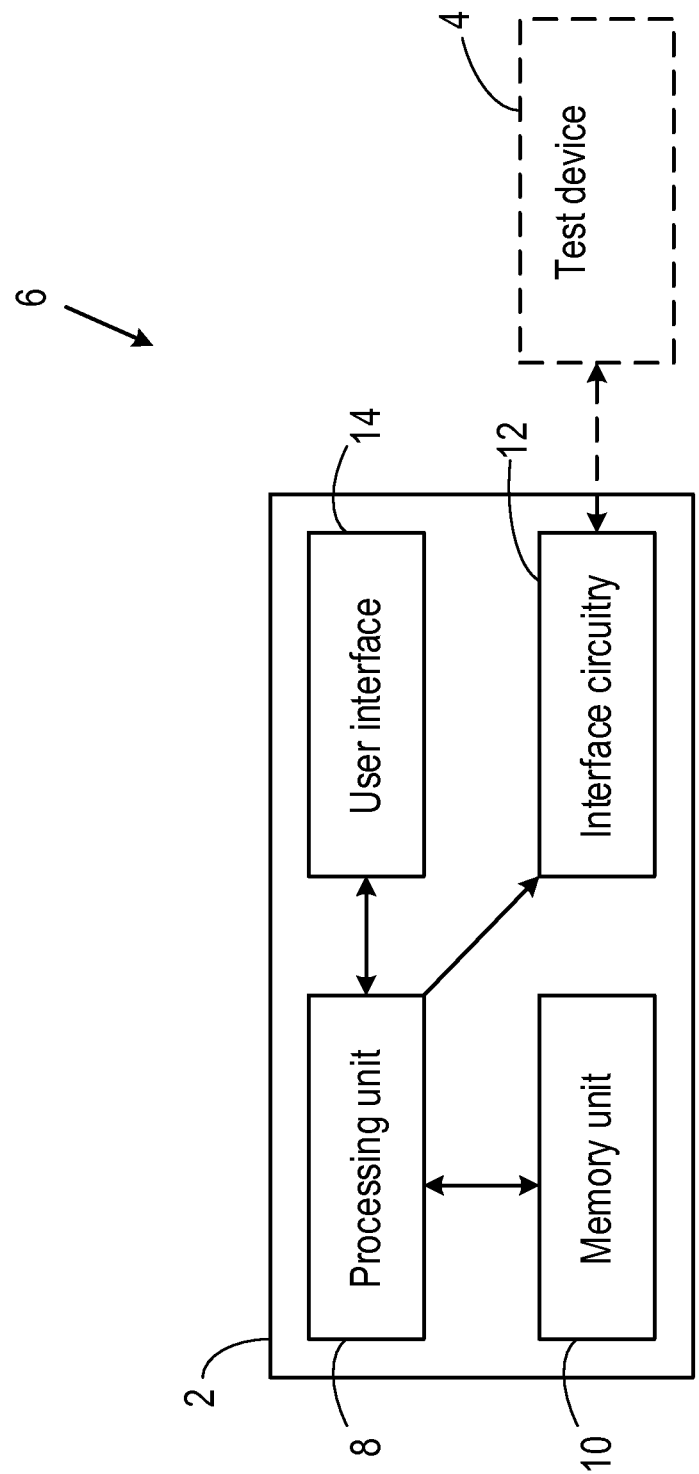
FIG. 1 is a block diagram of an apparatus and system according to an embodiment.

FIG. 1 shows a block diagram of an exemplary apparatus 2 that can be used in detecting malingering by a subject in tests of physical and/or mental function of the subject. It should be noted that the 'subject' referenced herein is the person or individual that is taking part in the activity or test. In some embodiments, the apparatus 2 can also be used by the subject to perform or complete the tests of physical and/or mental function. As such the apparatus 2 may be, or may comprise, a testing device for providing the physical and/or mental function tests. Alternatively, the apparatus 2 may be configured to be connected to a testing device 4 that provides the physical and/or mental function tests to form a system 6 for detecting malingering by a subject during the physical and/or mental function testing.

The testing device 4 (or the apparatus 2 in the embodiments where the apparatus 2 is used to provide the physical and/or mental function tests) can comprise a device or component that is used store physical and/or mental function test material, that can output required physical and/or mental function test material to a subject or to a separate device belonging to or used by the subject (such as a computer, tablet, smartphone, television, etc.), and that is used to receive and analyse the results of the inputs by the subject in response to the presented test. In some embodiments, the testing device 4 can be self-contained device (e.g. a computer, laptop, tablet computer, smart watch, smartphone, etc.) that stores the physical and/or mental function test material, presents the test to the subject (e.g. via a display screen), receives the inputs by the subject and analyses the results to provide a measure of the performance of the subject in the test. In some other embodiments, the testing device 4 can be a device or component (e.g. a computer, server, etc.) that stores the cognitive function test material, outputs the test material to a display device (e.g. a screen, a television, a smart phone, etc.), receives information representing the subject's inputs in response to the presented test and analyses the results to provide a measure of the performance of the subject in the test. In these embodiments, the testing device 4 can be a server that provides the test material to a web browser or application on the other device, and the subject's inputs returned to the server via the web browser or application for analysis and evaluation. It will be appreciated that the above embodiments also apply where the apparatus 2 is used to provide the cognitive function tests.

The apparatus 2 is an electronic device that comprises a processing unit 8 and a memory unit 10. The processing unit 8 is configured or adapted to control the operation of the apparatus 2 and to implement the techniques described herein for detecting malingering by a subject.

The processing unit 8 can be configured to execute or perform the methods described herein. The processing unit 8 can be implemented in numerous ways, with software and/or hardware, to perform the various functions described herein. The processing unit 8 may comprise one or more microprocessors or digital signal processor (DSPs) that may be programmed using software or computer program code to perform the required functions and/or to control components of the processing unit 8 to effect the required functions. The processing unit 8 may be implemented as a combination of dedicated hardware to perform some functions (e.g. amplifiers, pre-amplifiers, analog-to-digital convertors (ADCs) and/or digital-to-analog convertors (DACs)) and a processor (e.g., one or more programmed microprocessors, controllers, DSPs and associated circuitry) to perform other functions. Examples of components that may be employed in various embodiments of the present disclosure include, but are not limited to, conventional microprocessors, DSPs, application specific integrated circuits (ASICs), and field-programmable gate arrays (FPGAs).

The processing unit 8 is connected to a memory unit 10 that can store data, information and/or signals for use by the processing unit 8 in controlling the operation of the apparatus 2 and/or in executing or performing the methods described herein. In some implementations the memory unit 10 stores computer-readable code that can be executed by the processing unit 8 so that the processing unit 8, in conjunction with the memory unit 10, performs one or more functions, including the methods described herein. The memory unit 10 can comprise any type of non-transitory machine-readable medium, such as cache or system memory including volatile and non-volatile computer memory such as random access memory (RAM) static RAM (SRAM), dynamic RAM (DRAM), read-only memory (ROM), programmable ROM (PROM), erasable PROM (EPROM), and electrically erasable PROM (EEPROM).

The apparatus 2 also includes interface circuitry 12 for enabling a data connection to and/or data exchange with other devices, including any one or more of servers, databases, user devices, and one or more testing devices 4. The interface circuitry 12 can enable a connection between the apparatus 2 and a network, such as the Internet, via any desirable wired or wireless communication protocol. For example, the interface circuitry 12 can operate using WiFi, Bluetooth, Zigbee, or any cellular communication protocol (including but not limited to Global System for Mobile Communications (GSM), Universal Mobile Telecommunications System (UMTS), Long Term Evolution (LTE), LTE-Advanced, etc.). The interface circuitry 12 is connected to the processing unit 8.

In some embodiments, the apparatus 2 comprises a user interface 14 that includes one or more components that enables a user of apparatus 2 to input information, data and/or commands into the apparatus 2, and/or enables the apparatus 2 to output information or data to the user of the apparatus 2. As used herein, the 'user' of the apparatus can be a person, such as a neuropsychologist, that would like to determine if a test subject (referred to as a 'subject' or 'first subject' herein) is malingering. In embodiments where the apparatus 2 includes or is part of a testing device, the subject can also be considered as a user of the apparatus 2.

The user interface 14 can comprise any suitable input component(s), including but not limited to a keyboard, keypad, one or more buttons, switches or dials, a mouse, a track pad, a touchscreen, a stylus, a camera, a microphone, etc., and the user interface 14 can comprise any suitable output component(s), including but not limited to a display screen, one or more lights or light elements, one or more loudspeakers, a vibrating element, etc.

The apparatus 2 can be any type of electronic device or computing device. For example the apparatus 2 can be, or be part of, a server, a computer, a laptop, a tablet, a smartphone, etc.

It will be appreciated that a practical implementation of an apparatus 2 may include additional components to those shown in FIG. 1. For example the apparatus 2 may also include a power supply, such as a battery, or components for enabling the apparatus 2 to be connected to a mains power supply.

As noted above, a problem in detecting malingering in physical and/or mental function tests is that it can be useful to add specific malingering-related tests to the current test battery (i.e. a set of tests to be performed) in order to detect the malingering, but these tests can take a long time to complete and increase the overall time required for completing the physical and/or mental function tests. In addition, some tests may be useful in detecting some types of malingering, but not others. The techniques described herein therefore provide an approach by which a set of physical and/or mental function tests can be identified and used to test a subject's physical and/or mental function and also whether they may be malingering. A physical function test can test any aspect of physical function of a subject, including the gross motor skills/ability of the subject (e.g. ability to walk steadily, lift objects, etc.) and the fine motor skills/ability of the subject (e.g. relating to the functioning of the hands or fingers). A mental function test can test any aspect of mental function of a subject, including the cognitive functions of the subject, such as memory, perception, attention, motor skills, language, visual and spatial processing and executive functions. A test can include one or more activities that the subject is to perform and/or one or more questions that the subject is to answer.

Figure 2:
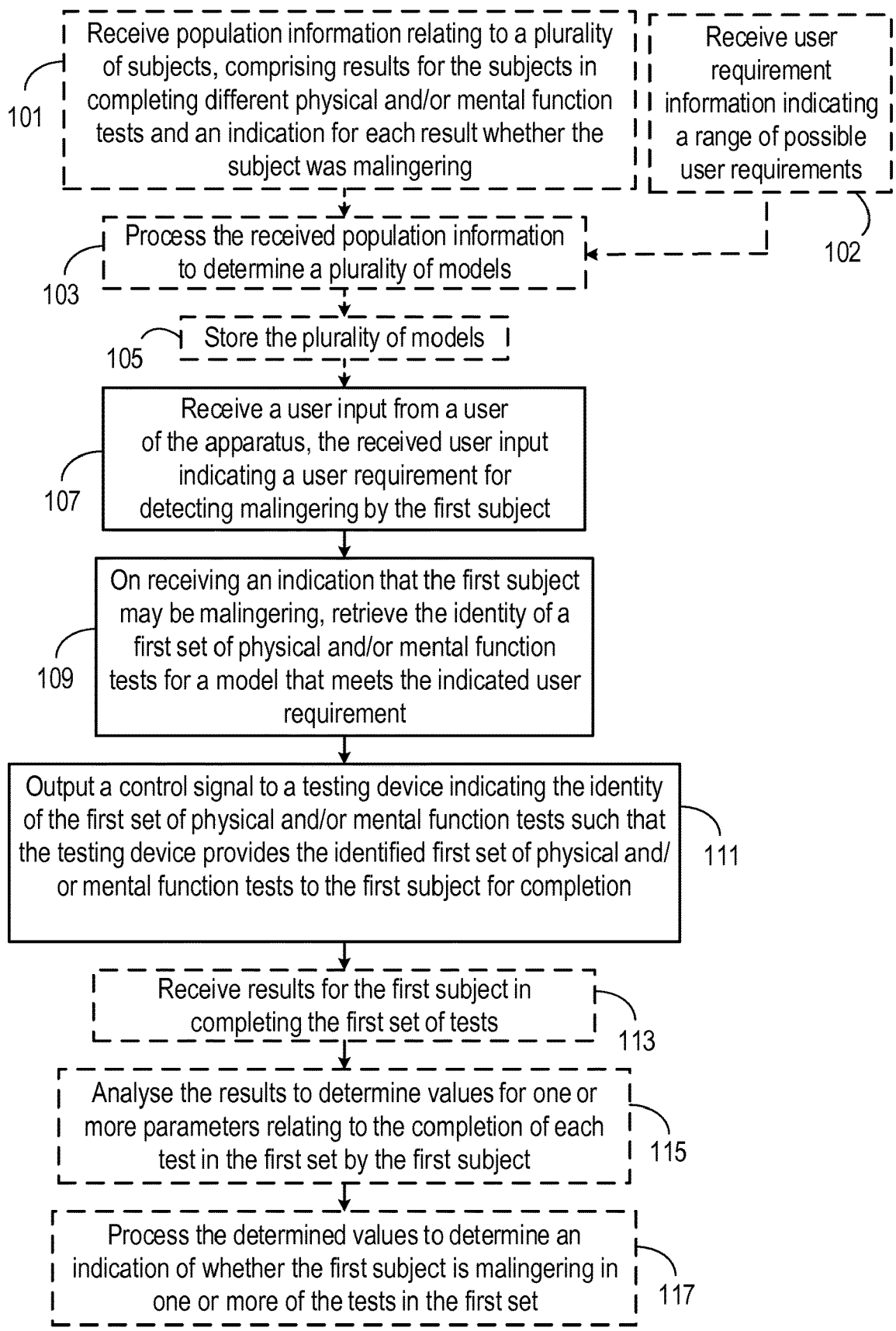
FIG. 2 is a flow chart illustrating an exemplary method according to an embodiment.

The flow chart in FIG. 2 shows a method for use in detecting malingering by a first subject according to various embodiments. Some or all of the steps in the method can be performed by the apparatus 2, for example by the processing unit 8 in conjunction with the memory unit 10. In that case, the processing unit 8 can be configured to perform the method, and/or the processing unit 8 can execute computer program code to cause the processing unit 8 to perform the method.

As noted below, the method according to the techniques described herein makes use of models that identify respective sets of physical and/or mental function tests that can be used to detect malingering by a subject. Steps 101-105 of the method in FIG. 2 relate to the generation of these models, and steps 107-117 relate to the selection and use of a model to detect malingering by the first subject. In some embodiments, the method is provided to identify respective sets of cognitive function tests that can be used to detect malingering by a subject in one or more cognitive function tests, and the following description can be interpreted accordingly.

In step 101, population information is received that relates to a plurality of subjects. The population information comprises results for the plurality of subjects in completing a plurality of different physical and/or mental function tests and an indication of whether the subject was malingering. The population information can include results for subjects that were malingering and subjects that were not malingering. The indication of whether a subject was malingering can be an indication that was provided by an assessor (e.g. neuropsychologist in the case of a mental and/or cognitive function assessment), provided by the results of a validated test for malingering or through an automated assessment of the performance for a test. The population information may be received from memory unit 10, or from a memory unit (e.g. a database) that is separate from the apparatus 2.

In step 102, user requirement information is received that indicates a range of possible user requirements for the models to be generated. The user requirements can relate to expectations of design and performance of the risk score models for different scenarios when different sets of physical and/or mental function tests are used for malingering detection. These expectations can be, for example, the range of quality metric values derivable from the tests, the number of tests used in the model, a minimum set of tests that should be used (e.g. identifying specific tests that should be part of the model), the reliability of the malingering indication, etc. For example the user can indicate that the models should have an AUC (area under the curve of a ROC (receiver operating characteristic) curve) of at least 85% or AUCs in the range 0.7 to 0.9, and/or that the maximum number of tests used in each scenario should be 15. The user requirement information can be received from the user of the apparatus 2, for example via the user interface 14.

Next, in step 103, the received population information and the received user requirement information is processed to determine the plurality of models. In this step, different scenarios are selected (e.g. each scenario having a respective set of values from the possible user requirements indicated in the user requirement information), and a set of physical and/or mental function tests are selected to form a model that meets the user requirements for each scenario. Thus the model will comprise or identify different physical and/or mental function test(s), which can be made up of physical and/or mental function test(s) of the same type but with different activities/questions (e.g. different arrangements of a set of numbers and/or letter in a trail making test, different mental arithmetic questions, etc.) and/or different types of physical and/or mental function tests (e.g. a trail making test, an F-score test in the MMPI, etc.), or a combination thereof, that can meet the user requirements when a subject performs the test(s). It will be appreciated that the model can be understood as a group or compilation of tests, also referred to as a 'test battery' or 'battery of tests'. In embodiments where tests may comprise one or more activities or questions, the model can be understood as a compilation of those one or more activities or questions into an overall test/test battery.

In some embodiments, the processing unit 8 is configured to process the received population information and user requirement information to determine the plurality of models using one or more artificial intelligence algorithms and/or one or more machine learning algorithms.

The received population information will include information for two groups of subjects, those that were malingering and those that were not malingering. The risk score models are trained using supervised machine learning algorithms (e.g., SLIM, Random Forest, Logistics Regression, Neural Networks, etc.) on these two groups to determine a set of physical and/or mental function tests that meet the user requirements for that scenario. For example, the schematic representation of a linear risk score model can be as follows:

$(x_1, y_1), \ldots, (x_N, y_N)$   Data $x_i = (1, x_{1i}, \ldots, x_{Pi}) \in \mathbb{R}^P$   Input variables $y_i \in \{-1, +1\}$   Outcome variable Model form $$\text{predict } \hat{y}_i = \begin{cases} +1 & \text{if } \lambda_1 x_{1i} + \lambda_2 x_{2i} + \ldots + \lambda_P x_{Pi} > \lambda_0 \\ -1 & \text{if } \lambda_1 x_{1i} + \lambda_2 x_{2i} + \ldots + \lambda_P x_{Pi} \leq \lambda_0 \end{cases}$$

where $\lambda_0$ is a threshold score, $\lambda_P$ are points for variable P, and $\lambda_1 x_{1i} + \lambda_2 x_{2i} + \ldots + \lambda_P x_{Pi}$ is the total score. Variable j not in model $\Leftrightarrow \lambda_j = 0$ and error on point I $\Leftrightarrow \hat{y}_i \neq y_i$.

determine$(\lambda_0, \lambda_1, \ldots \lambda_P)$   Goal

Once the models have been determined, the plurality of models are stored (step 105), for example in memory unit 10. Thus the models are stored, along with their corresponding quality metric values, and the information on the relevant user requirements (i.e. the user requirements that the models are appropriate for).

It will be appreciated that steps 101-105 can be performed in a set up phase for the apparatus 2, and thus steps 101-105 are typically not repeated frequently or repeated each time that a first subject is having their physical and/or mental function tested.

When a first subject is having their physical and/or mental function tested, or is about to have their physical and/or mental function tested, the user (e.g. neuropsychologist in the case of mental function or cognitive function tests) can provide a user input indicating one or more user requirements for detecting malingering in the first subject during those physical and/or mental function tests (step 107). This user input can be provided using the user interface 14. The one or more user requirements can comprise a level of reliability of detecting malingering, a number of physical and/or mental function tests in a set and/or an identity of one or more specific physical and/or mental function tests that the user would like the first subject to take.

For example, for a particular subject, the user can provide user requirements indicating that the first subject is to take a subset of tests 1-20 such that the AUC of the risk score is greater than 85%. For another subject, the user can provide user requirements indicating another subset of tests that can be used.

Step 109 occurs following receipt of an indication that the first subject may be malingering in one or more physical and/or mental tests, and in step 109 the identity of a first set of physical and/or mental function tests for a model in the plurality of models that meets the user requirements indicated in step 107 is retrieved from the memory unit 10. That is, if there is an indication that the first subject may be malingering, the memory unit 10 is searched to find a model that meets the user requirements, and the set of tests that make up this model are identified.

In some embodiments, the indication that the first subject may be malingering in the physical and/or mental test is received from the user of the apparatus 4, for example via the user interface 14. The user may provide this indication in response to observing the results of the first subject performing one or more tests, or the user can provide this indication for a first subject that is already suspected of malingering. In alternative embodiments, the indication that the first subject may be malingering in the physical and/or mental test is received from the testing device 4 (for example in response to the analysis of the performance of one or more physical and/or mental function tests by the first subject using the testing device 4). In another alternative embodiment, the processing unit 8 may receive a signal from the testing device 4 relating to the completion of one or more physical and/or mental function tests by the first subject (for example the signal can indicate the inputs by the first subject in performing the test), and the processing unit 8 can process the received signal to detect whether the first subject may be malingering. As noted above, ways in which malingering can be identified from particular tests are known in the art, and further details of this processing are not provided herein.

It will be appreciated that as an alternative approach to that shown in FIG. 2, step 107 can be performed after an indication is received that the first subject may be malingering. This can enable the user (e.g. neuropsychologist) to adapt their user requirements based on the current performance of the first subject (e.g. by specifying specific physical and/or mental function tests that should be used to test for malingering). For example, if a first subject has already taken several physical and/or mental function tests before the possible malingering indication is received, the user can provide a user requirement that indicates that a risk score model should be used that uses a maximum number of tests that have already been taken, along with additional tests to test for malingering, so as to minimise the use of test resources.

For example, if the user has provided a user requirement indicating that a subject that has already taken Tests 25, 30 and 34 should take a subset of tests 1-20 such that the AUC of the risk score model is greater than 85%, step 109 may provide a model that requires the subject to only additionally take tests 1-8, 10, and 13 and provide an AUC of 87%, or a model that uses all 20 tests with an AUC of 90%.

Once the model (and thus the identity of the physical and/or mental function tests for the model) has been identified in step 109, the apparatus 2 (processing unit 8) outputs a control signal to a testing device 4 indicating the identity of the first set of physical and/or mental function tests. This control signal causes the testing device 4 to provide the identified first set of physical and/or mental function tests to the first subject for completion to detect whether the first subject is malingering. Thus, for example, the control signal can cause the testing device 4 to output the relevant physical and/or mental function test material to the subject's device (e.g. to a web browser or application on a tablet, smartphone, etc.) for completion by the subject on that device.

After the first subject has performed the tests indicated in step 111, results are received for the first subject in completing the first set of physical and/or mental function tests (step 113). Step 113 (and the subsequent steps) can be performed by the apparatus 2, but it will be appreciated that in alternative embodiments the analysis of the results of the tests can be performed by a separate apparatus or device. The results can relate to the inputs provided by the first subject in completing the tests (e.g. the timing of each input, elements selected with the input, text/numbers input by the subject, etc.).

Next, the processing unit 8 analyses the results to determine values for one or more parameters relating to the completion of each physical and/or mental function test in the first set by the first subject (step 115). For example, in step 115 the processing unit 8 can determine scores or other metrics relating to the completion of the tests (e.g. an indication of how many tasks were completed correctly, an indication of whether the pace that the test was completed was within a normal range, an overall score for the test, etc.). In some embodiments, the processing unit 8 can analyse the results to determine values for parameters that can provide an indication of malingering (or not). As noted above, ways in which malingering can be identified from particular tests are known in the art, and further details of this processing are not provided herein.

FIG. 3 shows an exemplary set of results for one particular physical and/or mental function test, namely a digit span cognitive function test, with values for one or more parameters relating to the completion of the test. Thus, FIG. 3 shows the first subject's responses to several items, and indicates a score for each individual test element, a score for each item and an overall score.

It will be appreciated that the results for each test may be received in step 113 as that test is completed (i.e. before the next test is started) rather than receive the results for all tests at once. In that case, the analysis of the results in step 115 can be performed as each set of test results is received, or step 115 can be performed once the results for all of the tests in the first set of tests are received.

Next, in step 117, the processing unit 8 can process the determined values to determine an indication of whether the first subject is malingering in one or more of the physical and/or mental function tests in the first set. In some embodiments, the indication of whether the first subject is malingering can be a malingering score (denoted DMI) or malingering percentage, and can be formed by combining the determined values for the set of tests performed by the first subject. As with step 115, step 117 can be performed based on the results of the tests currently available, and step 117 can be repeated as more test results for the tests in the first set become available, which can improve the reliability of the indication of malingering over time.

The processing in step 117 can be performed in a number of different ways. For example, the determined values for the first subject can be compared to values determined for a population of healthy (and non-malingering) subjects, and pattern comparison algorithms used to determine a score indicating the level of similarity. In another example, the apparatus 2 can have previously been calibrated against a recognised validated malingerer test, such as the F-scale in the MMPI, so that the determined values can be directly coupled to a probability of malingering. In another example, weightings can be applied to determined values from different tests (for example based on how effective a particular test is at identifying malingering), and the weighted values combined to form the indication of whether the first subject is malingering.

In some cases the indication of whether the first subject is malingering (e.g. the malingering score) can be output to the user using the user interface 14. This can be seen in FIG. 3.

In some embodiments, the indication of whether the first subject is malingering can be compared to a threshold to determine if the first subject is malingering. For example, a malingering score above a threshold can indicate that the first subject is malingering, whereas a malingering score below the threshold can indicate that the first subject is not malingering, or that malingering has not been detected.

If the indication indicates that the first subject is malingering, the user may decide to stop the physical and/or mental function testing of the first subject. Alternatively, if the indication indicates that the first subject is malingering, the processing unit 8 may determine that the physical and/or mental function testing of the first subject should be stopped, and the processing unit 8 can send a suitable control signal to the testing device 4 to stop the tests.

FIG. 4 shows a display output that can be provided to the user of the apparatus 2 that indicates the results of several different cognitive/mental function tests in the first set of tests. Thus, the set of tests includes the digit span test, verbal fluency test, trail making test, Rey-O test, O-search test and WCS test, and five malingering measures (P1-P5) are shown for each test, with the level of shading indicating the standard deviations away from the score expected for the subject if no malingering is present, along with the overall malingering score (DMI) and an optional display element that shows an indication provided by the user of the apparatus 2 as to whether the first subject is malingering.

If the indication determined in step 117 suggests that the first subject is not malingering, then the test results can be treated accordingly by the user (e.g. the results can be considered as representative of the physical and/or mental function of the first subject).

However, if the indication determined in step 117 is inconclusive on whether the first subject is malingering, for example if the malingering score is quite high (but without exceeding a threshold) and/or the user is not able to make their own determination of whether the first subject is malingering, then the user can be requested or prompted to provide a different set of user requirements to those provided in step 107. This request or prompt can be provided using the user interface 14. The user can then provide an indication of a different user requirement, again via the user interface 14. The different user requirement may be a different number of tests for the subject to take, different ones of the tests to include or exclude from the set of tests, a different malingering detection reliability, etc. Based on the different user requirement, the identity of a second set of physical and/or mental function tests for a model that meets the indicated different user requirement can be retrieved from the memory unit 10. This step can be performed in a similar way to step 109 above. A control signal is then output to the testing device 4 indicating the retrieved identity of the second set of physical and/or mental function tests (similar to step 111 above). Therefore the testing device 4 provides the identified second set of physical and/or mental function tests to the first subject for completion to detect whether the first subject is malingering. The results of the second set of tests can be analysed in the same way as the results of the first set of tests as described above in steps 113-115.

Alternatively, if the indication determined in step 117 is inconclusive on whether the first subject is malingering, for example if the malingering score is quite high (but without exceeding a threshold) and/or the user is not able to make their own determination of whether the first subject is malingering, the processing unit 8 can be configured to determine that a difficulty level of one or more of the physical and/or mental function tests in the first set of physical and/or mental function tests is to be increased. By increasing the difficulty level of the test, this may make it harder for a malingering subject to disguise their malingering behaviour. It is also possible to consider the response curve to varying difficulty level and from this deduce whether malingering is present. Those skilled in the art will be aware of ways in which the difficulty level of particular physical and/or mental function tests can be increased (or decreased), and further details are not provided herein. If the difficulty level of any tests is to be increased, the processing unit 8 can output a control signal to the testing device 4 indicating the identity of the first set of physical and/or mental function tests and the increased difficulty level. The testing device 4 can therefore provide the identified first set of physical and/or mental function tests to the first subject at the increased difficulty level, and an indication of whether the first subject is malingering can be determined as described above.

Thus, the techniques described above provide that if there is any indication that a first subject may be malingering, a suitable set of physical and/or mental function tests are identified and used to test the first subject. In embodiments where an overall indication of the malingering (e.g. a score) is provided after each test, the user (e.g. neuropsychologist) can have the option to stop the tests, and/or the apparatus 2 can stop the tests if the overall indication of malingering exceeds a threshold (optionally also if a quality metric (e.g. AUC) for the malingering indication is above a threshold).

Variations to the disclosed embodiments can be understood and effected by those skilled in the art in practicing the principles and techniques described herein, from a study of the drawings, the disclosure and the appended claims. In the claims, the word "comprising" does not exclude other elements or steps, and the indefinite article "a" or "an" does not exclude a plurality. A single processor or other unit may fulfil the functions of several items recited in the claims. The mere fact that certain measures are recited in mutually different dependent claims does not indicate that a combination of these measures cannot be used to advantage. A computer program may be stored or distributed on a suitable medium, such as an optical storage medium or a solid-state medium supplied together with or as part of other hardware, but may also be distributed in other forms, such as via the Internet or other wired or wireless telecommunication systems. Any reference signs in the claims should not be construed as limiting the scope.

The invention claimed is:

1. An apparatus for use in detecting malingering by a first subject in a test of physical and/or mental function of the first subject, the apparatus comprising:
   a processor;
   a non-transitory computer readable medium that stores instructions, which when executed by the processor causes the processor to:
   receive population information relating to a plurality of subjects, comprising results for the plurality of subjects resulting from completing different mental and/or physical function tests, and an indication for each result whether a subject is malingering;
   receive a user input from a user of the apparatus, the received user input indicating a user requirement for detecting malingering by the first subject;
   process the received population information to determine a plurality of models;
   following receipt of an indication that the first subject may be malingering in one or more physical and/or mental function tests, retrieve, from the non-transitory computer readable medium, an identity of a first set of physical and/or mental function tests for a model in the instructions that meets the indicated user requirement;
   identify a respective set of physical and/or mental function tests from a plurality of different physical and/or mental function tests used to detect malingering by a subject and that meets one or more possible user requirements for detecting malingering; and
   output a control signal to a testing device indicating the retrieved identity of the first set of physical and/or mental function tests such that the testing device provides the identified first set of physical and/or mental function tests to the first subject for completion.

2. The apparatus as claimed in claim 1, wherein the one or more possible user requirements comprises a level of reliability of detecting malingering and/or a number of physical and/or mental function tests in a set.

3. The apparatus as claimed in claim 1, wherein the indication that the first subject may be malingering in the physical and/or mental function test is received from the user of the apparatus, or received from the testing device.

4. The apparatus as claimed in claim 1, wherein the processor is configured to receive the indication that the first subject may be malingering by:
   receiving a signal from the testing device relating to the completion of a physical and/or mental function test by the first subject; and
   processing the received signal to detect whether the first subject may be malingering.

5. The apparatus as claimed in claim 1, wherein the processor is further configured to:
   receive results for the first subject in completing the first set of physical and/or mental function tests;
   analyse the results to determine values for one or more parameters relating to the completion of each physical and/or mental function test in the first set by the first subject; and
   process the determined values to determine an indication of whether the first subject is malingering in one or more of the physical and/or mental function tests in the first set.

6. The apparatus as claimed in claim 1, wherein the processor is further configured to:
   receive user requirement information indicating a range of possible user requirements; and
   process the received population information and the received user requirement information to determine the instructions.

7. The apparatus as claimed in claim 1, wherein the processor is further configured to:
   in response to an indication indicating that the identified first set of physical and/or mental function tests did not detect whether the first subject is malingering, prompt the user of the apparatus to indicate a different user requirement for detecting malingering by the first subject;
   in response to receiving an indication of a different user requirement from the user, retrieve, from the non-transitory computer readable medium, the identity of a second set of physical and/or mental function tests for a model that meets the indicated different user requirement; and
   output a control signal to a function testing device indicating the retrieved identity of the second set of physical and/or mental function tests such that the function testing device provides the identified second set of physical and/or mental function tests to the first subject for completion.

8. The apparatus as claimed in claim 1, wherein the processor is further configured to:
   in response to an indication indicating that the identified first set of physical and/or mental function tests did not detect whether the first subject is malingering, determine that a difficulty level of one or more of the physical and/or mental function tests in the first set of physical and/or mental function tests is to be increased; and
   output a control signal to the testing device indicating the identity of the first set of physical and/or mental function tests and the increased difficulty level such that the testing device provides the identified first set of physical and/or mental function tests to the first subject for completion.

9. The apparatus as claimed in claim 1, wherein the apparatus further comprises the testing device.

10. A computer-implemented method for use in detecting malingering by a first subject in a test of physical and/or mental function of the first subject, the method comprising:
   storing a plurality of models in a non-transitory computer readable medium, each model identifying a respective set of physical and/or mental function tests from a plurality of different physical and/or mental function tests used to detect malingering by a subject and that meets one or more possible user requirements for detecting malingering;
   receiving population information relating to a plurality of subjects, comprising results for the plurality of subjects resulting from completing different mental and/or physical function tests, and an indication for each result whether a subject is malingering;
   receiving a user input from a user of the apparatus, the received user input indicating a user requirement for detecting malingering by the first subject;
   processing the received population information to determine a plurality of models;
   following receipt of an indication that the first subject may be malingering in one or more physical and/or mental tests, retrieving, from the non-transitory computer readable medium, the identity of a first set of physical and/or mental function tests for a model that meets the indicated user requirement; and outputting a control signal to a testing device indicating the retrieved identity of the first set of physical and/or mental function tests such that the testing device provides the identified first set of physical and/or mental function tests to the first subject for completion.

11. The computer-implemented method as claimed in claim 10, wherein the one or more possible user requirements comprises a level of reliability of detecting malingering and/or a number of physical and/or mental function tests in a set.

12. The computer-implemented method as claimed in claim 10, wherein the method further comprises:
receiving results for the first subject in completing the first set of physical and/or mental function tests;
analysing the results to determine values for one or more parameters relating to the completion of each physical and/or mental function test in the first set by the first subject; and
processing the determined values to determine an indication of whether the first subject is malingering in one or more of the physical and/or mental function tests in the first set.

13. The computer-implemented method as claimed in claim 10, wherein the method further comprises:
in response to an indication indicating that the identified first set of physical and/or mental function tests did not detect whether the first subject is malingering, prompting the user of an apparatus to indicate a different user requirement for detecting malingering by the first subject;
in response to receiving an indication of a different user requirement from the user, retrieving, from the non-transitory computer readable medium, the identity of a second set of physical and/or mental function tests for a model that meets the indicated different user requirement; and
outputting a control signal to the testing device indicating the retrieved identity of the second set of physical and/or mental function tests such that the testing device provides the identified second set of physical and/or mental function tests to the first subject for completion to detect whether the first subject is malingering.

14. A non-transitory computer readable medium that stores computer readable code, which when executed by a processor, causes the processor to:
identify a respective set of physical and/or mental function tests from a plurality of different physical and/or mental function tests used to detect malingering by a subject and that meets one or more possible user requirements for detecting malingering;
receiving population information relating to a plurality of subjects, comprising results for the plurality of subjects resulting from completing different mental and/or physical function tests, and an indication for each result whether a subject is malingering;
processing the received population information to determine a plurality of models;
receive a user input from a user of an apparatus, the received user input indicating a user requirement for detecting malingering by a first subject;
following receipt of an indication that the first subject may be malingering in one or more physical and/or mental function tests, retrieve, from the non-transitory computer readable medium, an identity of a first set of physical and/or mental function tests for a model comprising computer readable code that meets the indicated user requirement; and
output a control signal to a testing device indicating the retrieved identity of the first set of physical and/or mental function tests such that the testing device provides the identified first set of physical and/or mental function tests to the first subject for completion.

15. The non-transitory computer readable medium as claimed in claim 14, wherein the one or more possible user requirements comprises a level of reliability of detecting malingering and/or a number of physical and/or mental function tests in a set.

16. The non-transitory computer readable medium as claimed in claim 14, wherein the indication that the first subject may be malingering in the physical and/or mental function test is received from the user of the apparatus, or received from the testing device.

17. The non-transitory computer readable medium as claimed in claim 14, wherein the computer readable code, when executed by the processor are adapted to receive the indication that the first subject may be malingering by:
receiving a signal from the testing device relating to the completion of a physical and/or mental function test by the first subject; and
processing the received signal to detect whether the first subject may be malingering.

18. The non-transitory computer readable medium as claimed in claim 14, wherein the computer readable code, when executed by the processor further cause the processor to:
receive results for the first subject in completing the first set of physical and/or mental function tests;
analyse the results to determine values for one or more parameters relating to the completion of each physical and/or mental function test in the first set by the first subject; and
process the determined values to determine an indication of whether the first subject is malingering in one or more of the physical and/or mental function tests in the first set.

19. The non-transitory computer readable medium as claimed in claim 14, wherein the computer readable code, when executed by the processor further cause the processor to:
in response to an indication indicating that the identified first set of physical and/or mental function tests did not detect whether the first subject is malingering, prompt the user of the apparatus to indicate a different user requirement for detecting malingering by the first subject;
in response to receiving an indication of a different user requirement from the user, retrieve, from the non-transitory computer readable medium, the identity of a second set of physical and/or mental function tests for a model that meets the indicated different user requirement; and
output a control signal to a function testing device indicating the retrieved identity of the second set of physical and/or mental function tests such that the function testing device provides the identified second set of physical and/or mental function tests to the first subject for completion.

* * * * *